United States Patent [19]

Lee et al.

[11] Patent Number: 5,358,961
[45] Date of Patent: Oct. 25, 1994

[54] PYRROLIDINE DERIVATIVES

[75] Inventors: Ki Hong Lee; Dong Soo Kim, both of Seoul; Il Hwan Ryu, Kangweon-Do; Man Keun Kim; Kwan Ho Lee, both of Seoul, all of Rep. of Korea

[73] Assignee: Jin Ro Limited, Seoul, Rep. of Korea

[21] Appl. No.: 84,268

[22] PCT Filed: Nov. 24, 1992

[86] PCT No.: PCT/KR92/00066
§ 371 Date: Nov. 15, 1993
§ 102(e) Date: Nov. 15, 1993

[87] PCT Pub. No.: WO93/11136
PCT Pub. Date: Jun. 10, 1993

[30] Foreign Application Priority Data

Nov. 30, 1991 [KR] Rep. of Korea .................. 91-21842
Nov. 30, 1991 [KR] Rep. of Korea .................. 91-21843

[51] Int. Cl.⁵ .......................... A61K 31/40; C07F 9/02
[52] U.S. Cl. ........................................ 514/423; 548/413
[58] Field of Search ........................... 548/413; 514/423

[56] References Cited

U.S. PATENT DOCUMENTS 4,468,519 8/1984 Krapcho ........................ 548/409

*Primary Examiner*—Johann Richter
*Assistant Examiner*—Joseph K. McKane
*Attorney, Agent, or Firm*—Kenyon & Kenyon

[57] ABSTRACT

This invention relates to new pyrrolidine derivatives represented by formula (I) as below, having superior pharmacological activity as antihypertensive agents

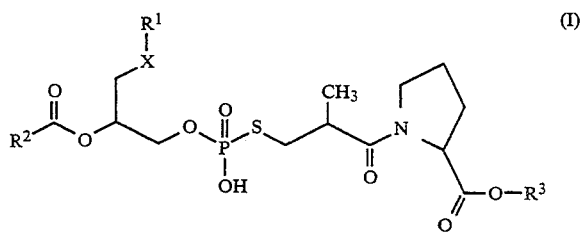

wherein $R^1$ is saturated or unsaturated alkyl of 2 to 20 carbon atoms, or aryl group;

$R^2$ is saturated or unsaturated alkyl of 1 to 17 carbon atoms, or aryl group;

$R^3$ is hydrogen atom, saturated or unsaturated alkyl of 1 to 20 carbon atoms, or aryl group or its derivatives: and X is oxygen or sulfur atom.

18 Claims, No Drawings

PYRROLIDINE DERIVATIVES

This application is a 371 of PCT/KR 92.00066 filed Nov. 24, 1992.

TECHNICAL FIELD

This invention relates to new pyrrolidine derivatives represented by general formula(I) as below and their pharmacologically acceptable salts which are useful as antihypertensive

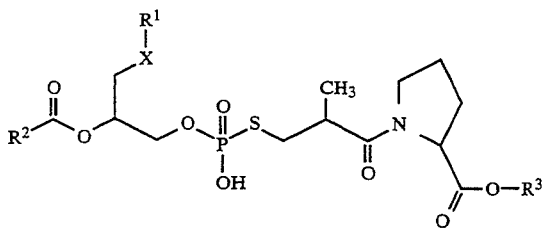

wherein, $R^1$ is saturated or unsaturated alkyl of 2 to 20 carbon atoms, or aryl group;

$R^2$ is saturated or unsaturated alkyl of 1 to 17 carbon atoms, or aryl group;

$R^3$ is hydrogen atom, saturated or unsaturated alkyl of 1 to 20 carbon atoms, or aryl group or its derivatives; and X is oxygen or sulfur atom.

BACKGROUND OF THE INVENTION

Platelet activating factor(PAF) was first identified in 1979 to be 1-O-alkyl-2-O-acetyl-sn-glycerol-3-phosphocholine by Benveniste et al. [C. R. Acad. Sci., Paris(D), 289, 1037–1040(1979)].

It was also reported that this PAF produces a variety of physiological responses such as platelet activation and antihypertension. The conjugates of nucleosides with PAF derivatives or with their analogues have been reported to exhibit diverse pharmacological activities such as anticancer, antiinflammation and antivirus activity in literatures [Journal of Medicinal Chemistry, 25, 1322(1982), Biochemical and Biophysical Research Communication, 85, 715(1978), Biochemica et Biophysica Acta, 69, 604(1980), J. Med. Chem., 28(2), 171-7(1985), Ibid., 31(9), 1793-8(1988), Ibid., 33(5), 1380-6(1990)].

Most of the antihypertensive agents, so far used in medicine have to be taken orally or by intravenous administration and the dosage has to be repeatedly administered to maintain proper plasma concentration of a drug.

However to achieve and maintain a plasma concentration of drug within the therapeutical range is not easy. If the plasma concentration of drug remains high it leads to related side effects and development of tolerance to the drug. The problem of economy of long term oral therapy also cannot be disregarded.

Development of transdermal therapeutic mode of delivery of antihypertensive agent with favorable pharmacokinetic parameters maintained for a long duration time, with improved convenience and patient compliance, and with minimal side effects has been for long considered necessary.

SUMMARY OF THE INVENTION

The objective of this invention is to provide new pyrrolidine derivative antihypertensive compounds with convenient dosage regime compared to convenient therapy, and superior therapeutic effect.

DETAILED DESCRIPTION OF THE INVENTION

This invention relates to new pyrrolidine derivatives shown by above formula (I) and especially new compounds having excellent physiological activities as antihypertensive agent.

In the above formula(I), $R^1$ is octadecyl, cetyl, methyl, ethyl, dodecyloxy, methylphenyl or sulfonyloctyl group; $R^2$ is methyl, ethyl, propyl, butyl, heptadecyl, pentadecyl, oleyl or cetyl group; $R^3$ is hydrogen, methyl, ethyl, propyl, isopropyl, butyl, pentyl, cyclohexyl, benzoyl, benzyl, p-nitrobenzyl, p-toluenesulfonyl, p-methoxybenzyl, 2,4,6-trimethylbenzyl or phthalimidomethyl group.

The phospholipid part of above formula(I) consists either D, L or DL type of optical isomers and the part linked to phosphoric acid am angiotensin converting enzyme(ACE) inhibitors and their derivatives commonly used as antihypertensive agent.

Present invention also includes the compositions of above reffered structure(1) antihypertensive agents in pharmaceutical dosage forms including transdermal therapeutic dosage form.

New pyrrolidine derivatives of this invention represented by formula(I) are new conjugates introducing ACE inhibitor into basic structure of glycerol. Specifically, conjugates of 1-S- or 1-O-alkyl-2-O-acyl phospholipids are linked with ACE inhibitors or their derivatives by phosphate ester bond and resulting compounds are new synthetic compounds with favorable antihypertensive activity.

The methods for preparing new compounds of this invention are as follows;

New pyrrolidine derivatives and their salts of above formula(I) can be prepared by condensation of compound(II) with compound of formula(III) using condensing agent in anhydrous basic solvent

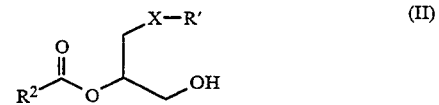

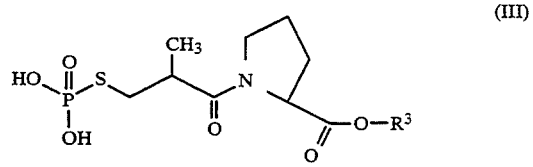

wherein, $R^1$ and $R^2$ each are as defined in formula(I) above; and $R^3$ is saturated or unsaturated alkyl of 1 to 20 carbon atoms, or aryl group or its derivatives.

The products of formula (I) are produced by the method depicted in the following equations.

1-S-alkyl-2-O-acylthioglycerol or 1-O-alkyl-2-O-acylglycerol(II) is condensed with phosphoric acid compound(III) to give compound(I). Using the metallic catalyst, e.g., zinc, iron and nickel, formula (I) can be converted by conventional methods such as hydrolysis or hydrogenation to formula(I')

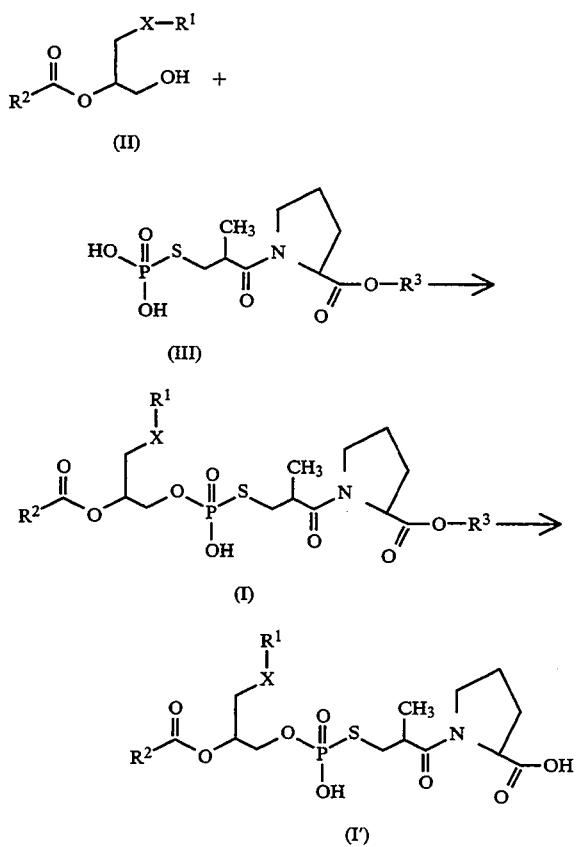

wherein,
$R^1$, $R^2$ and $R^3$ are as defined previously.

In this invention the condensation reaction is conducted at 40°~100° C. But it shall be noted that higher temperature of reaction lead to unnecessary side reaction and if the reaction temperature is kept low, the reaction does not proceed.

Within the scope of this invention, anhydrous bases are pyridine, triethylamine and ethylamine, etc. The condensing agents in this synthetic route are dicyclohexylcarbodiimide, 2,4,6-triisopropylbenzenesulfonylchloride, 1-(2,4,6-triisopropylbenzene-sulfonyl)imidazole, 1-(2,4,6-triisopropylbenzenesulfonyl)-3-nitro-1,2,4-triazole and 2-ethoxy-1-(2H)-quinoline carboxylic acid ester.

The compounds of formula (I) and their salts in this invention can be used in pharmaceutical formulations in combination with organic or inorganic vehicles. Their salts are physiologically acceptable conventional salts. They may be utilized in conventional types of pharmaceutical dosage forms such as suspensions, emulsions, patches, powders, granules, capsules, tablets and pills, containing commonly used components of pharmaceutical formulation, vehicle, preservative, stabilizer, dispersant and adjuvants such as damping agent, emulsifier, filler or buffer, colorant, etc., can be used.

In accordance with this invention, they can be formulated into patches, specially for transdermal therapeutic application.

Illustrative of new compound of formula (I) by this invention are the following: rac-1-O-cetyl-2-O-acetylglyceryl-3-phosphoryl captopril-p-nitrobenzyl ester, rac-1-O-cetyl-2-O-acetylglyceryl-3-phosphoryl captopril ethyl ester, rac-1-O-cetyl-2-O-acetylglyceryl-3-phosphoryl captopril methyl ester, rac-1-O-cetyl-2-O-acetylglyceryl-3-phosphoryl captopril benzyl ester, rac-1-O-cetyl-2-O-acetylglyceryl-3-phosphoryl captopril benzoyl ester, rac-1-O-cetyl-2-O-acetylglyceryl-3-phosphoryl captopril isopropyl ester, rac-1-O-cetyl-2-O-acetylglyceryl-3-phosphoryl captopril-n-butyl ester, rac-1-O-cetyl-2-O-acetylglyceryl-3-phosphoryl captopril-t-butyl ester, rac-1-O-cetyl-2-O-acetylglyceryl-3-phosphoryl captopril cyclohexyl ester, rac-1-O-cetyl-2-O-acetylglyceryl-3-phosphoryl captopril pentyl ester, rac-1-O-cetyl-2-O-acetylglyceryl-3-phosphoryl captopril-p-toluenesulfonyl ester, rac-1-O-cetyl-2-O-acetylglyceryl-3-phosphoryl captopril-p-methoxybenzyl ester, rac-1-O-cetyl-2-O-acetylglyceryl-3-phosphoryl captopril-2,4,6-trimethylbenzyl ester, rac-1-O-cetyl-2-O-acetylglyceryl-3-phosphoryl captopril phthalimido methyl ester, rac-1-O-oleyl-2-O-palmitoylglyceryl-3-phosphoryl captopril-p-nitrobenzyl ester, rac-1-O-oleyl-2-O-palmitoylglyceryl-3-phosphoryl captopril ethyl ester, rac-1-O-oleyl-2-O-palmitoylglyceryl-3-phosphoryl captopril methyl ester, rac-1-O-oleyl-2-O-palmitoylglyceryl-3-phosphoryl captopril benzyl ester, rac-1-O-oleyl-2-O-palmitoylglyceryl-3-phosphoryl captopril benzoyl ester, rac-1-O-oleyl-2-O-palmitoylglyceryl-3-phosphoryl captopril isopropyl ester, rac-1-O-oleyl-2-O-palmitoylglyceryl-3-phosphoryl captopril-n-butyl ester, rac-1-O-oleyl-2-O-palmitoylglyceryl-3-phosphoryl captopril-t-butyl ester, rac-1-O-oleyl-2-O-palmitoylglyceryl-3-phosphoryl captopril cyclohexyl ester, rac-1-O-oleyl-2-O-palmitoylglyceryl-3-phosphoryl captopril pentyl ester, rac-1-O-oleyl-2-O-palmitoylglyceryl-3-phosphoryl captopril-p-toluenesulfonyl ester, rac-1-O-oleyl-2-O-palmitoylglyceryl-3-phosphoryl captopril-p-methoxybenzyl ester, rac-1-O-oleyl-2-O-palmitoylglyceryl-3-phosphoryl captopril-2,4,6-trimethylbenzyl ester, rac-1-O-oleyl-2-O-palmitoylglyceryl-3-phosphoryl captopril phthalimido methyl ester, rac-1-O-oleyl-2-O-acetylglyceryl-3-phosphoryl captopril-p-nitrobenzyl ester, rac-1-O-oleyl-2-O-acetylglyceryl-3-phosphoryl captopril ethyl ester, rac-1-O-oleyl-2-O-acetylglyceryl-3-phosphoryl captopril methyl ester, rac-1-O-oleyl-2-O-acetylglyceryl-3-phosphoryl captopril benzylester, rac-1-O-oleyl-2-O-acetylglyceryl-3-phosphoryl captopril benzoyl ester, rac-1-O-oleyl-2-O-acetylglyceryl-3-phosphoryl captopril isopropyl ester, rac-1-O-oleyl-2-O-acetylglyceryl-3-phosphoryl captopril-n-butyl ester, rac-1-O-oleyl-2-O-acetylglyceryl-3-phosphoryl captopril-t-butyl ester, rac-1-O-oleyl-2-O-acetylglyceryl-3-phosphoryl captopril cyclohexyl ester, rac-1-O-oleyl-2-O-acetylglyceryl-3-phosphoryl captopril pentyl ester, rac-1-O-oleyl-2-O-acetyl glyceryl-3-phosphoryl captopril-p-toluenesulfonyl ester, rac-1-O-oleyl-2-O-acetylglyceryl-3-phosphoryl captopril-p-methoxybenzyl ester, rac-1-O-oleyl-2-O-acetylglyceryl-3-phosphoryl captopril-2,4,6-trimethylbenzyl ester, rac-1-O-oleyl-2-O-acetylglyceryl-3-phosphoryl captopril phthalimido methyl ester, rac-1-O-octadecyl-2-O-palmitoylglyceryl-3-phosphoryl captopril-p-nitrobenzyl ester, rac-1-O-octadecyl-2-O-palmitoylglyceryl-3-phosphoryl captopril ethyl ester, rac-1-O-octadecyl-2-O-palmitoylglyceryl-3-phosphoryl captopril methyl ester, rac-1-O-octadecyl-2-O-palmitoylglyceryl-3-phosphoryl captopril benzyl ester, rac-1-O-octadecyl-2-O-palmitoylglyceryl-3-phosphoryl captopril benzoyl ester, rac-1-O-octadecyl-2-O-palmitoylglyceryl-3-phosphoryl captopril isopropyl ester, rac-1-O-octadecyl-2-O-palmitoylglyceryl-3-phosphoryl captopril-n-butyl ester, rac-1-O-octadecyl-2-O-palmitoylglyceryl-3-phosphoryl captopril-t-butyl ester, rac-1-O-octadecyl-2-O-palmitoylglyceryl-3-phosphoryl captopril cyclohexyl ester, rac-1-O-octadecyl-2-O-palmitoylglyceryl-3-phosphoryl captopril pentyl ester, rac-1-O-octadecyl-2-O-palmitoylglyceryl-3-phosphoryl captopril-p-toluenesulfonyl ester, rac-1-O-octadecyl-2-O-palmitoylglyceryl-3-phosphoryl captopril-p-methoxybenzyl ester, rac-1-O-octadecyl-2-O-palmitoylglyceryl-3-phosphoryl captopril-2,4,6-trimethylbenzyl ester, rac-1-O-octadecyl-2-O-palmitoylglyceryl-3-phosphoryl captopril phthalimido methyl ester, rac-1-O-octadecyl-2-O-acetylglyceryl-3-phosphoryl captopril-p-nitrobenzyl ester, rac-1-O-octadecyl-2-O-acetylglyceryl-3-phosphoryl captopril ethyl ester, rac-1-O-octadecyl-2-O-acetylglyceryl-3-phosphoryl captopril methyl ester, rac-1-O-octadecyl-2-O-acetylglyceryl-3-phosphoryl captopril benzyl ester, rac-1-O-octadecyl-2-O-acetylglyceryl-3-phosphoryl captopril benzoyl ester, rac-1-O-octadecyl-2-O-acetylglyceryl-3-phosphoryl captopril isopropyl ester, rac-1-O-octadecyl-2-O-acetylglyceryl-3-phosphoryl captopril-n-butyl ester, rac-1-O-octadecyl-2-O-acetylglyceryl-3-phosphoryl captopril-t-butyl ester, rac-1-O-octadecyl-2-O-acetylglyceryl-3-phosphoryl captopril cyclohexyl ester, rac-1-O-octadecyl-2-O-acetylglyceryl-3-phosphoryl captopril pentyl ester, rac-1-O-octadecyl-2-O-acetylglyceryl-3-phosphoryl captopril-p-toluenesulfonyl ester, rac-1-O-octadecyl-2-O-acetylglyceryl-3-phosphoryl captopril-p-methoxybenzylester, rac-1-O-octadecyl-2-O-acetylglyceryl-3-phosphoryl captopril-2,4,6-trimethylbenzyl ester, rac-1-O-octadecyl-2-O-acetylglyceryl-3-phosphoryl captopril phthalimido methyl ester, rac-1-S-cetyl-2-O-acetylthioglyceryl-3-phosphoryl captopril-p-nitrobenzyl ester, rac-1-S-cetyl-2-O-acetylthioglyceryl-3-phosphoryl captopril ethyl ester, rac-1-S-cetyl-2-O-acetylthioglyceryl-3-phosphoryl captopril methyl ester, rac-1-S-cetyl-2-O-acetylthioglyceryl-3-phosphoryl captopril benzyl ester, rac-1-S-cetyl-2-O-acetylthioglyceryl-3-phosphoryl captopril benzoyl ester, rac-1-S-cetyl-2-O-acetylthioglyceryl-3-phosphoryl captopril isopropyl ester, rac-1-S-cetyl-2-O-acetylthioglyceryl-3-phosphoryl captopril-n-butyl ester, rac-1-S-cetyl-2-O-acetylthioglyceryl-3-phosphoryl captopril-t-butyl ester, rac-1-S-cetyl-2-O-acetylthioglyceryl-3-phosphoryl captopril cyclohexyl ester, rac-1-S-cetyl-2-O-acetylthioglyceryl-3-phosphoryl captopril pentyl ester, rac-1-S-cetyl-2-O-acetylthioglyceryl-3-phosphoryl captopril-p-toluenesulfonyl ester, rac-1-S-cetyl-2-O-acetylthioglyceryl-3-phosphoryl captopril-p-methoxybenzyl ester, rac-1-S-cetyl-2-O-acetyl thioglyceryl-3-phosphoryl captopril-2,4,6-trimethylbenzyl ester, rac-1-S-cetyl-2-O-acetylthioglyceryl-3-phosphoryl captopril-phthalimido methyl ester, rac-1-S-oleyl-2-O-palmitoylthioglyceryl-3-phosphoryl captopril-p-nitrobenzyl ester, rac-1-S-oleyl-2-O-palmitoylthioglyceryl-3-phosphoryl captopril ethyl ester, rac-1-S-oleyl-2-O-palmitoylthioglyceryl-3-phosphoryl captopril methyl ester, rac-1-S-oleyl-2-O-palmitoylthioglyceryl-3-phosphoryl captopril benzyl ester, rac-1-S-oleyl-2-O-palmitoylthioglyceryl-3-phosphoryl captopril benzoyl ester, rac-1-S-oleyl-2-O-palmitoylthioglyceryl-3-phosphoryl captopril isopropyl ester, rac-1-S-oleyl-2-O-palmitoylthioglyceryl-3-phosphoryl captopril-n-butyl ester, rac-1-S-oleyl-2-O-palmitoylthioglyceryl-3-phosphoryl captopril-t-butyl ester, rac-1-S-oleyl-2-O-palmitoylthioglyceryl-3-phosphoryl captopril cyclohexyl ester, rac-1-S-oleyl-2-O-palmitoylthioglyceryl-3-phosphoryl captopril pentyl ester, rac-1-S-oleyl-2-O-palmitoylthioglyceryl-3-phosphoryl captopril-p-toluenesulfonyl ester, rac-1-S-oleyl-2-O-palmitoylthioglyceryl-3-phosphoryl captopril-p-methoxybenzyl ester, rac-1-S-oleyl-2-O-palmitoylthioglyceryl-3-phosphoryl captopril-2,4,6-trimethylbenzyl ester, rac-1-S-oleyl-2-O-palmitoylthioglyceryl-3-phosphoryl captopril phthalimido methyl ester, rac-1-S-oleyl-2-O-acetylthioglyceryl-3-phosphoryl captopril-p-nitrobenzyl ester, rac-1-S-oleyl-2-O-acetylthioglyceryl-3-phosphoryl captopril ethyl ester, rac-1-S-oleyl-2-O-acetylthioglyceryl-3-phosphoryl captopril methyl ester, rac-1-S-oleyl-2-O-acetylthioglyceryl-3-phosphoryl captopril benzyl ester, rac-1-S-oleyl-2-O-acetylthioglyceryl-3-phosphoryl captopril benzoyl ester, rac-1-S-oleyl-2-O-acetylthioglyceryl-3-phosphoryl captopril isopropyl ester, rac-1-S-oleyl-2-O-acetylthioglyceryl-3-phosphoryl captopril-n-butyl ester, rac-1-S-oleyl-2-O-acetylthioglyceryl-3-phosphoryl captopril-t-butyl ester, rac-1-S-oleyl-2-O-acetylthioglyceryl-3-phosphoryl captopril cyclohexyl ester, rac-1-S-oleyl-2-O-acetylthioglyceryl-3-phosphoryl captopril pentyl ester, rac-1-S-oleyl-2-O-acetylthioglyceryl-3-phosphoryl captopril-p-toluenesulfonyl ester, rac-1-S-oleyl-2-O-acetylthioglyceryl-3-phosphoryl captopril-p-methoxybenzyl ester, rac-1-S -oleyl-2-O-acetylthioglyceryl-3-phosphoryl captopril-2,4,6-trimethylbenzyl ester, rac-1-S-oleyl-2-O-acetylthioglyceryl-3-phosphoryl captopril phthalimido methyl ester, rac-1-S-octadecyl-2-O-palmitoylthioglyceryl-3-phosphoryl captopril-p-nitrobenzyl ester, rac-1-S-octadecyl-2-O-palmitoylthioglyceryl-3-phosphoryl captopril ethyl ester, rac-1-S-octadecyl-2-O-palmitoylthioglyceryl-3-phosphoryl captopril methyl ester, rac-1-S-octadecyl-2-O-palmitoylthioglyceryl-3-phosphoryl captopril benzyl ester, rac-1-S-octadecyl-2-O-palmitoylthioglyceryl-3-phosphoryl captopril benzoyl ester, rac-1-S-octadecyl-2-O-palmitoylthioglyceryl-3-phosphoryl captopril isopropyl ester, rac-1-S-octadecyl-2-O-palmitoylthioglyceryl-3-phosphoryl captopril-n-butyl ester, rac-1-S-octadecyl-2-O-palmitoylthioglyceryl-3-phosphoryl captopril-t-butyl ester, rac-1-S-octadecyl-2-O-palmitoylthioglyceryl-3-phosphoryl captopril cyclohexyl ester, rac-1-S-octadecyl-2-O-palmitoylthioglyceryl-3-phosphoryl captopril pentyl ester, rac-1-S-octadecyl-2-O-palmitoylthioglyceryl-3-phosphoryl captopril-p-toluenesulfonyl ester, rac-1-S-octadecyl-2-O-palmitoylthioglyceryl-3-phosphoryl captopril-p-methoxybenzyl ester, rac-1-S-octadecyl-2-O-palmitoylthioglyceryl- 3-phosphoryl captopril-2,4,6-trimethylbenzyl ester, rac-1-S-octadecyl-2-O-palmitoylthioglyceryl-3-phosphoryl captopril phthalimido methyl ester, rac-1-S-octadecyl-2-O-acetylthioglyceryl-3-phosphoryl captopril-p-nitrobenzyl ester, rac-1-S-octadecyl-2-O-acetylthioglyceryl-3-phosphoryl captopril ethyl ester, rac-1-S-octadecyl-2-O-acetylthioglyceryl-3-phosphoryl captopril methyl ester, rac-1-S-octadecyl-2-O-acetylthioglyceryl-3-phosphoryl captopril benzyl ester, rac-1-S-octadecyl-2-O-acetylthioglyceryl-3-phosphoryl captopril benzoyl ester, rac-1-S-octadecyl-2-O-acetylthioglyceryl-3-phosphoryl captopril isopropyl ester, rac-1-S-octadecyl-2-O-acetylthioglyceryl-3-phosphoryl captopril-n-butyl ester, rac-1-S-octadecyl-2-O-acetylthioglyceryl-3-phosphoryl captopril-t-butyl ester, rac-1-S-octadecyl-2-O-acetylthioglyceryl-3-phosphoryl captopril cyclohexyl ester, rac-1-S-octadecyl-2-O-acetylthioglyceryl-3-phosphoryl captopril pentyl ester, rac-1-S-octadecyl-2-O-acetylthioglyceryl-3-phosphoryl captopril-p-toluenesulfonyl ester, rac-1-S-octadecyl-2-O-acetylthioglyceryl-3-phosphoryl captopril-p-methoxybenzyl ester, rac-1-S-octadecyl-2-O-acetylthioglyceryl-3-phosphoryl captopril-2,4,6-trimethylbenzyl ester, rac-1-S-octadecyl-2-O-acetylthioglyceryl-3-phosphoryl captopril phthalimido methyl ester, or their pharmacologically acceptable salts.

In this invention, the most important point for development of transdermal therapeutic agent is to increase the absorption through transdermal route. Because the skin cell membrane of the human body consists of phospholipid layer, the lipophilic compounds have greater propensity to be absorbed from skin to the body.

These conjugates represented in this invention can easily penetrate through skin cell consisting of double layer of phospholipid, because these compounds are phospholipid conjugates with lipophilic physicochemical properties. It is also possible to maintain steady, ideal plasma concentrate of these drugs, because of the inherent mechanism of transdermal controlled delivery of a drug.

The absorbed material through the skin is hydrolized to ACE inhibitor and phospholipid part by lysophospholiphase in the body. The phospholipid part is converted to the platelet activating factor via a biosynthesis route and then it express blood pressure regulatory action and the ACE inhibitor part of the molecule exhibits its blood pressure lowering activity by inhibiting the conversion of angiotensin I to angiotensin II.

Therefore, because each component of hydrolized phospholipid and ACE inhibitor conjugate has blood pressure controlling function, new compounds having two parts are expected to possess favorable pharmacological activity and also have superior blood pressure lowering activity.

The following examples are detailed illustrative of this invention.

EXAMPLE 1

Rac-1-O-octadecyl-2-O-palmitoyl-glyceryl-3-phosphoryl captopril-p-nitrobenzyl ester Dissolve 4.55 g (0.01 tool) of 3-S-thiophosphoryl-2-D-methylpropanoyl-L-proline-p-nitrobenzyl ester and 7 g (0.012 mol) of rac-1-O-octadecyl-2-O-palmitoyl-glycerol in 350 ml of anhydrous pyridine and concentrate to 2/3 of volume in vacuo. 6.8 g (0.033 mol) of dicyclohexylcarbodiimide is added, the mixture is heated at 75~80° C. for 4 days, then concentrate reaction mixture in vacuo.

To the residue 600 ml of ethyl ether and 350 ml of distilled water are added. Then the solution is adjusted the pH to 0~1 with 10 ml of 10% hydrochloric acid and stirred overnight. Filter, then the organic phase is dried and concentrated in vacuo. Chromatography with chloroform-methanol(9:1) mixture affords 3.61 g of the desired product.

m.p.:44°~45° C.
TLC $R_f$0.45 (chloroform:methanol=5:1)
NMR (CDCl$_3$)δ0.87(6, t, 2CH$_3$), 1.10–1.57(61, m, 29CH$_2$, CH$_3$), 2.03(2, t, CH$_2$CO), 2.30(2, t, CH$_2$CO), 3.05–3.25(4, t, OCH$_2$, proline NCH$_2$), 3.45(2, t, OCH$_2$), 3.62–3.75(4, m, CH$_2$O, SCH$_2$), 3.85–4.20(2, d, CH$_2$OP), 4.70(1, t, proline CH), 5.16–5.26(3, m, CCHC, benzyl CH$_2$), 7.52(2, d, C$_6$H$_4$), 8.20(2, d, C$_6$H$_4$)
IR: (KBr) 2918, 2850, 1739, 1641, 1525, 1346, 1168, 1078 cm$^{-1}$

EXAMPLE 2

Rac-1-O-octadecyl-2-O-palmitoyl-glyceryl-3-phosphoryl captopril

Dissolve 0.5 g (0.5 mmol) of rac-1-O-octadecyl-2-O-palmitoyl-3-phosphorylcaptopril-p-nitrobenzyl ester in 30 ml of methylenechloride and add 180 ml of 1N sulfuric acid solution, 20 ml of methanol, and 2.2 g of zinc powder. After stirring overnight, wash the reaction mixture with 80 ml of distilled water. Dry on anhydrous sodium sulfate, filter through celite, concentrate in vacuo. After purification by preparative thin layer chromatography with chloroform-methanol (5:1). 0.28 g(yield 64.94%) of white powder is obtained as the desired product. m.p.:66°~68° C.
TLC $R_f$0.45 (chloroform:methanol=3:1)
NMR (CDCl$_3$)δ0.87(6, t, 2CH$_3$), 1.11–1.65(61, m, 29CH$_2$, CH$_3$), 1.85–2.17(2, t, CH$_2$CO), 2.35(2, t, CH$_2$CO), 2.95–3.75(12, m, CH$_2$CH$_2$, proline NCH$_2$, OCH$_2$, CH$_2$O, SCH$_2$), 3.45(2, t, OCH$_2$), 3.62–3.75(4, m, CH$_2$O, SCH$_2$), 3.85–4.02(2, d, CH$_2$OP), 4.18(1, t, proline CH), 5.19(1, m, CCHC)
IR:(KBr) 3379, 2918, 2850, 1737, 1610, 1170, 1078 cm$^{-1}$

EXAMPLE 3

Rac-1-O-octadecyl-2-O-acetyl-glyceryl-3-phosphoryl captopril-p-nitrobenzyl ester Dissolve 8.52 g (19.71 mmol) of 3-S-thiophosphoryl-2-D-methylpropanoyl-L-proline-p-nitrobenzyl ester and 7.9 g (20.43 mmol) of rac-1-O-octadecyl-2-O-acetylglycerol in 400 ml of anhydrous pyridine and concentrate to 2/3 of volume in vacuo.

After adding 12 g (63.38 mmol) of dicyclohexylcarbodiimide, the reaction mixture is heated at 70°~80° C. for 4 days and concentrate in vacuo.

To the residue 600 ml of ethyl ether and 350 ml of distilled water are added. Then mixture is adjusted the pit to 0~1 with 30 ml of 10% hydrochloric acid and stirred overnight. Filter, then the organic phase is dried and concentrated in vacuo. Chromatography with chloroform-methanol(9:1) affords 3.18 g of yellow amorphous powder as the desired product.
m.p.:37°~38° C.
TLC $R_f$0.35 (chloroform:methanol=5:1)
NMR (CDCl$_3$)δ0.87(6, t, 2CH$_3$), 1.12–1.57(35, m, 16CH$_2$, CH$_3$), 1.73–2.40(7, m, CH$_2$CH$_2$, CH$_3$CO), 2.61–3.15(4, m, OCH$_2$, proline NCH$_2$), 3.49–4.18(2, m, OCH$_2$, CH$_2$O, SCH$_2$, CH$_2$OP), 4.61(1, t, proline CH), 5.16–5.38(3, m, CCHC, benzyl CH$_2$), 7.52(2, d, C$_6$H$_4$), 8.20(2, d, C$_6$H$_4$)
IR: (KBr) 2922, 2852, 1739, 1639, 1525, 1346, 1240, 1166, 1076 cm$^{-1}$

EXAMPLE 4

Rac-1-O-octadecyl-2-O-acetyl-glyceryl-3-phosphoryl captopril

Dissolve 0.43 g (0.53 mmol) of rac-1-O-octadecyl-2-O-acetyl glyceryl-3-phosphoryl captopril-p-nitrobenzyl ester in 30 ml of methylenechloride and add 180 ml of 1N sulfuric acid solution, 20 ml of methanol, and 3.2 g of zinc powder. After stirring overnight, wash reaction mixture with 80 ml of distilled water. Dry on anhydrous sodium sulfate, filter through celite, concentrate in vacuo. After purification by preparative thin layer chromatography with chloroform-methanol (5:1), 0.26 g(yield 72.63%) of white powder is obtained as the desired product.

m.p.: 58°~60° C.

TLC R$_f$0.10 (chloroform: methanol=3:1)

NMR (CDCl$_3$)δ0.87(3, t, CH$_3$), 1.11–1.65(35, m, 16CH$_2$, CH$_3$), 1.85–2.30(7, m, CH$_2$CH$_2$, CH$_3$CO), 2.95–3.75(8, m, OCH$_2$, proline NCH$_2$, CH$_2$O, SCH$_2$), 3.85–4.15(2, d, CH$_2$OP), 4.28(1, t, proline CH), 5.19(1, m, CCHC)

IR: (KBr) 3373, 2918, 2850, 1737, 1606, 1240, 1078 cm$^{-1}$

EXAMPLE 5

Rac-1-S-octadecyl-2-O-palmitoyl-thioglyceryl-3-phosphoryl captopril-p-nitrobenzyl ester Dissolve 0.32 g (10 mmol) of 3-S-thiophosphoryl-2-D-methylpropanoyl-L-proline-p-nitrobenzyl ester and 5.97 g (10 mmol) of rac-1-S-octadecyl-2-O-palmitoyl-1-thioglycerol in 350 ml of anhydrous pyridine and concentrate to 2/3 of volume in vacuo. After adding 6.8 g (33 mmol) of dicyclohexylcarbodiimide, reaction mixture is heated at 70° C. to 80° C. for 4 days and concentrate in vacuo.

To the residue in 500 ml of ethyl ether and 300 ml of distilled water are added. Then mixture is adjusted the pH to 0~1 with 20 ml of 10% hydrochloric acid and stirred overnight. Filter, then the organic phase is dried and concentrate in vacuo. Chromatography with chloroform-methanol(9:1) affords 1.6 g(yield 15.79%) of pale yellow powder as the desired product m.p. : 46°~47° C.

TLC R$_f$0.52 (chloroform: methanol=5:1)

NMR (CDCl$_3$)δ0.89(6, t, 2CH$_3$), 1.10–1.65(61, m, 29CH$_2$, CH$_3$), 2.03(7, m, CH$_2$CH$_2$, CH$_3$CO), 2.23–2.89(6, m, CH$_2$CO, CH$_2$SCH$_2$), 3.04(2, m, proline NCH$_2$), 3.65–3.80(2, m, SCH$_2$), 4.40(2, d, CH$_2$OPCH$_2$OP), 4.68(1, t, proline CH), 5.11–5.35(3, m, CCHC, benzyl CH$_2$), 7.52(2, d, C$_6$H$_4$), 8.20(2, d, C$_6$H$_4$)

IR: (KBr) 2918, 2850, 1737, 1641, 1525, 1348, 1170, 1078 cm$^{-1}$

EXAMPLE 6

Rac-1-S-octadecyl-2-O-palmitoyl-thioglyceryl-3-phosphoryl captopril

Dissolve 0.5 g (0.49 retool) of rac-1-S-octadecyl-thioglyceryl-3-phosphorylcaptopril-p-nitrobenzyl ester in 30ml of methylenechloride and add 180 ml of 1N sulfuric acid solution, 20 ml of methanol, and 2.2 g of zinc powder. After stirring overnight, wash the reaction mixture with 80 ml of distilled water, dry on anhydrous sodium sulfate, filter through celite, concentrate in vacuo. After purification by preparative thin layer chromatography with chloroform-methanol (5:1), 0.12 g(yield 27.88%) of white powder is obtained as the desired product.

m.p.: 68°~70° C.

TLC R$_f$0.47 (chloroform: methanol=3:1)

NMR (CDCl$_3$)δ0.88(6, t, 2CH$_3$), 1.12–1.65(61, m, 29CH$_2$, CH$_3$), 1.85–2.27(4, m, CH$_2$CH$_2$), 2.35(2, t, CH$_2$CO), 2.45–2.90(5, m, CH$_2$S'CH$_2$, CCHCO), 3.04(2, m, proline NCH$_2$), 3.65(2, m, SCH$_2$), 4.05(2, d, CH$_2$OP), 4.31(1, t, proline CH), 5.19(1, m, CCHC)

IR: (KBr) 3373, 2918, 2850, 1737, 1604, 1076 cm$^{-1}$

EXAMPLE 7

Rac-1-S-octadecyl-2-O-acetyl-thioglyceryl-3-phosphoryl captopril-p-nitrobenzyl ester Dissolve 5.6 g (12.95 mmol) of 3-S-thiophosphoryl-2-D-methylpropanoyl-L-proline-p-nitrobenzyl ester and 5.33 g (13.23 retool) of rac-1-S-octadecyl-2-O-acetylthioglycerol in 300 ml of anhydrous pyridine and concentrate to 2/3 of volume in vacuo. After adding 7.8 g (37.80 mmol) of dicyclohexylcarbodiimide, the reaction mixture is heated at 70°~80° C. for 4 days and concentrate in vacuo.

To the residue in 600 ml of ethyl ether and 350 ml of distilled water are added. Then the mixture is adjusted the pH to 0~1 with 30 ml of 10% hydrochloric acid and stirred overnight. Filter, then the organic phase is dried and concentrate in vacuo. Chromatography with chloroform-methanol(9:1) affords 1.2 g(yield 11.34%) of yellow amorphous powder as the desired product.

m.p.: 35°~36° C.

TLC R$_f$0.38(chloroform:methanol=5:1)

NMR (CDCl$_3$)δ0.87(3, t, CH$_3$), 1.10–1.63(35, m, 16CH$_2$, CH$_3$), 1.92–2.40(7, m, CH$_2$CH$_2$, CH$_3$CO), 2.52(4, t, CH$_2$SCH$_2$), 2.61–3.15(2, m, proline NCH$_2$), 3.65–3.80(2, m, SCH$_2$), 4.00(2, d, CH$_2$OP), 4.68(1, t, proline CH, 5.11–5.35(3, m, CCHC, benzyl CH$_2$), 7.52(2, d, C$_6$H$_4$), 8.20(2, d, C$_6$H$_4$)

IR: (KBr)2922, 2852, 1739, 1641, 1523, 1346, 1167, 1074 cm$^{-1}$

EXAMPLE 8

Rac-1-S-octadecyl-2-O-acetyl-thioglyceryl-3-phosphoryl captopril

Dissolve 0.3 g (0.36 mmol) of rac-1-S-octadecyl-2-O-acetyl-thioglyceryl-3-phosphorylcaptopril-p-nitrobenzyl ester in 30 ml of methylenechloride and add 180 ml of 1N sulfuric acid solution, 20 ml of methanol, and 2.2 g of zinc powder. After stirring overnight, wash the reaction mixture with 80 ml of distilled water. Dry on anhydrous sodium sulfate, filter through celite, concentrate in vacuo. After purification by preparative thin layer chromatography with chloroform-methanol (5:1), 0.11 g(yield 43.96%) of white powder is obtained as the desired product.

m.p.: 61°~63° C.

TLC R$_f$0.12(chloroform: methanol=3:1)

NMR (CDCl$_3$)δ0.88(3, t, CH$_3$), 1.13–1.65(35, m, 16CH$_2$, CH$_3$), 1.81–2.35(7, m, CH$_2$CH$_2$, CH$_3$CO),2.52(4, m, CH$_2$SCH$_2$), 2.70–3.10(2, m, proline NCH$_2$,), 3.65–3.80(2, m, SCH$_2$), 4.00(2, d, CH$_2$OP), 4.32(1, t, proline CH), 5.12(1, m, CCHC)

IR: (KBr) 3373, 2918, 2850, 1739, 1610, 1078 cm$^{-1}$

EXPERIMENTAL EXAMPLE

The inhibitory activity of angiotensin converting enzyme for the compounds of this invention prepared by above examples was determined as follows;

The inhibitory activity was determined by using a modification of the method of Cushman, et al. [Biochemical Pharmacology, 20, 1637(1971)] Rabbit lung acetone powder was extracted with 10 volumes of 50 mM sodium borate buffer solution(pH 8.3) by homogenization at 4° C. and centrifuged for 40 minutes at 40,000 ×g.

The supernatant which contained angiotensin converting enzyme was used for ACE assay. Hippuryl-L-histidyl-L-leucine(HHL) was used as a substrate of enzymatic reaction and the reaction was determined in 13×100 mm of test tube.

The assay mixture (total volume, 0.25 ml) consisted of 50 mM sodium borate buffer (pH 8.3), 300 mM sodium chloride, and 5 mM HHL(pH 8.3), and they were reacted by addition of 0~10 mU of rabbit lung acetone powder extract for 30 minutes at 37° C.

The volume of enzyme extract was 0.15 ml or below and the reaction solution was preincubated at 37° C. for 30 minutes without the substrate and after adding HHL reacted for 30 minutes, the reaction was terminated by addition of 0.25 ml of 1N-HCl aqueous solution.

In the case of blank assay, hydrochloric acid was added before adding the enzyme extract. Hippuric acid was extracted with 1.5 ml of ethyl acetate which was separated by centrifuging at 3,000 rpm for 10 minutes. 1.0ml of ethyl acetate layer was transferred into the test tube and evaporated at 90° C. for 1 hour on temp-block.

Hippuric acid was dissolved in 1.0 ml of 50 mM sodium borate buffer (pH 8.3) and qualified from its absorbance at 228 nm. The final concentration of inhibitor was adjusted to $2\times10^{-4}$, $2\times10^{-5}$ μM with sodium borate buffer solution(pH 8.3) and reaction solution without the substrate was preincubated for 30 minutes and after adding the substrate, it was reacted at 37° C. for 30 minutes and terminated with 1N-HCl.

The synthesized inhibitors with non-water soluble property were dissolved by ultrasonic treatment. Angiotensin convening enzyme inhibitory activity is compared with captopril.

[TEST RESULTS]

The test results obtained for the compound of example 1, 2, 3, 4, 5, 6, 7 and 8 are shown in table below:

| Example No. of Compound | Concentration (μM) $2\times10^{-4}$ | $2\times10^{-5}$ |
|---|---|---|
| Compound 1 | 77% | 39% |
| Compound 2 | 97% | 80% |
| Compound 3 | 85% | 60% |
| Compound 4 | 98% | 98% |
| Compound 5 | 31% | 4% |
| Compound 6 | 92% | 70% |
| Compound 7 | 78% | 43% |
| Compound 8 | 90% | 80% |
| Captopril | 94% | 91% |

Compound 1: rac-1-O-octadecyl-2-O-palmitoyl-glyceryl-3-phosphorylcaptopril-p-nitrobenzyl ester Compound 2: rac-1-O-octadecyl-2-O-palmitoyl-glyceryl-3-phosphoryl captopril Compound 3: rac-1-O-octadecyl-2-O-acetyl-glyceryl-3-phosphoryl captopril-p-nitrobenzyl ester Compound 4: rac-1-O-octadecyl-2-O-acetyl-glyceryl-3-phosphoryl captopril Compound 5: rac-1-S-octadecyl-2-O-palmitoyl-thioglyceryl-3-phosphoryl captopril-p-nitrobenzyl ester Compound 6: rac-1-S-octadecyl-2-O-palmitoyl-thioglyceryl-3-phosphoryl captopril Compound 7: rac-1-S-octadecyl-2-O-acetyl-thioglyceryl-3-phosphoryl captopril-p-nitrobenzyl ester Compound 8: rac-1-S-octadecyl-2-O-acetyl-thioglyceryl-3-phosphoryl captopril.

From the results above expressed it can be concluded that the new compounds mentioned in this invention possess antihypertensive activity at least equivalent to that of captopril and these compounds have lipophilic activity which permits their transdermal delivery resulting in superior antihypertensive effect.

What is claimed is:

1. Pyrrolidine derivatives and salts represented by formula (I) as below wherein, R$^1$ is saturated or unsaturated alkyl of 2 to 20 carbon atoms, or aryl group;

R$^2$ is saturated or unsaturated alkyl of 1 to 17 carbon atoms, or aryl group;

R$^3$ is hydrogen atom, saturated or unsaturated alkyl of 1 to 20 carbon atoms, or aryl group and X is oxygen or sulfur atom.

2. The pyrrolidine derivatives according to claim 1, wherein R$^1$ is octadecyl, oleyl, cetyl, methyl, ethyl, dodecyloxy, methylphenyl or sulfonyloctyl group.

3. The pyrrolidine derivatives according to claim 1, wherein R$^2$ is methyl, ethyl, propyl, butyl, heptadecyl, pentadecyl, oleyl or cetyl.

4. The pyrrolidine derivatives according to claim 1, wherein R$^3$ is hydrogen, methyl, ethyl, propyl, isopropyl, butyl, pentyl,cyclohexyl, benzoyl, benzyl, p-nitrobenzyl, toluenesulfonyl, p-methoxybenzyl, 2,4,6-trimethylbenzyl or phthalimidomethyl group.

5. The pyrrolidine derivatives attending to claim 1, wherein the compound of formula (I) is rac-1-O-octadecyl-2-O-palmitoylglyceryl-3-phosphoryl captopril-p-nitrobenzyl ester.

6. The pyrrolidine derivatives according to claim 1, wherein the compound of formula (I) is rac-1-S-octadecyl-2-O-palmitoylthioglyceryl-3-phosphoryl captopril-p-nitrobenzyl ester.

7. The pyrrolidine derivatives according to claim 1, wherein the compound of formula (I) is rac-1-O-octadecyl-2-O-palmitoylglyceryl-3-phosphoryl captopril.

8. The pyrrolidine derivatives according to claim 1, wherein the compound of formula (I) is rac-1-S-octadecyl-2-O-palmitoylthioglyceryl-3-phosphoryl captopril.

9. The pyrrolidine derivatives according to claim 1, wherein the compound of formula (I) is rac-1-O-octadecyl-2-O-acetylglyceryl-3-phosphoryl captopril-p-nitrobenzyl ester.

10. The pyrrolidine derivatives according to claim 1, wherein the compound of formula (I) is rac-1-S-octadecyl-2-O-acetylthioglyceryl-3-phosphoryl captopril-p-nitrobenzyl ester.

11. The pyrrolidine derivatives according to claim 1, wherein the compound of formula (I) is rac-1-O-octadecyl-2-O-acetylglyceryl-3-phosphoryl captopril.

12. The pyrrolidine derivatives according to claim 1, wherein the compound of formula (I) is rac-1-S-octadecyl-2-O-acetylthioglyceryl-3-phosphoryl captopril.

13. A method for preparing new pyrrolidine derivatives or their salts of formula (I) by condensation of compound of formula (II) with compound of formula (III) in anhydrous basic solvent using condensing agent.

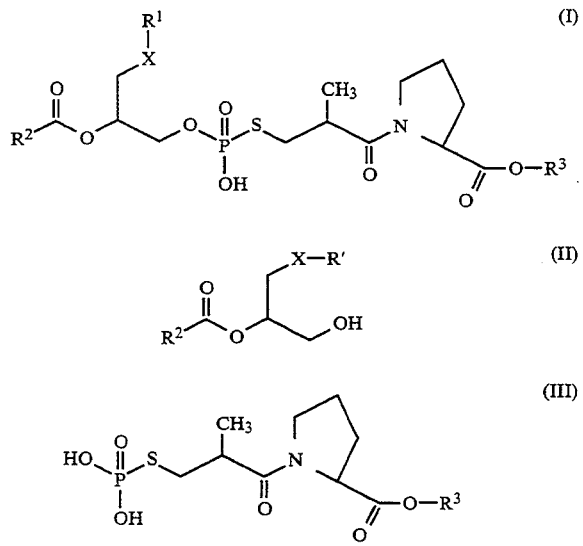

wherein,

R¹, R², R³ and X each are as defined in claim 1.

14. The method according to claim 13, wherein pyridine, triethylamine or ethylamine is used as anhydrous base.

15. The method according to claim 13, wherein dicyclohexylcarbodiimide, 2,4,6-triisopropylbenzenesulfonylchloride, 1-(2,4,6-triisopropylbenzenesulfonyl) imidazole, 1-(2,4,6-triisoproylbenzenesulfonyl)-3-nitro-1,2,4-triazole or 2-ethoxy-1-(2H)-quinoline carboxylic acid ester is used as condensing agent.

16. The method according to claim 13, wherein said condensation is carried out at 40°~100° C.

17. A pharmaceutical composition useful in the treatment of hypertension having pyrrolidine derivatives and their salts of formula(I) as below

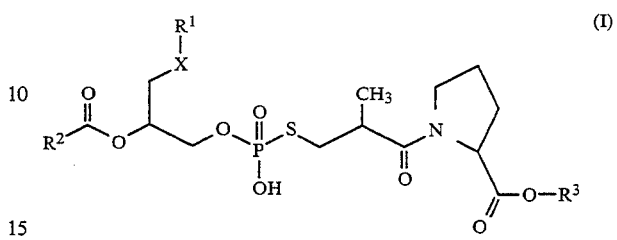

wherein,

R¹, R², R³ and X each are as defined in claim 1.

18. A formulation for transdermal administration having pyrrolidine derivatives or their salts of formula (I) as a pharmacologically active component for antihypertension

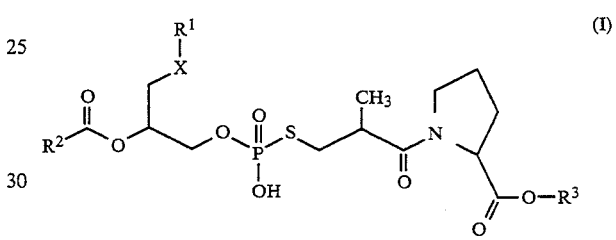

wherein,

R¹, R², R³ and X each are as defined in claim 1.

* * * * *